United States Patent
Marchionni et al.

(10) Patent No.: US 9,416,085 B2
(45) Date of Patent: Aug. 16, 2016

(54) PROCESS FOR THE MANUFACTURE OF FLUOROSURFACTANTS

(75) Inventors: Giuseppe Marchionni, Milan (IT); Vito Tortelli, Milan (IT)

(73) Assignee: SOLVAY SPECIALTY POLYMERS ITALY S.P.A., Bollate (Milan) (IT)

( * ) Notice: Subject to any disclaimer, the term of this patent is extended or adjusted under 35 U.S.C. 154(b) by 886 days.

(21) Appl. No.: 13/002,779

(22) PCT Filed: Jul. 7, 2009

(86) PCT No.: PCT/EP2009/058536
§ 371 (c)(1),
(2), (4) Date: Apr. 27, 2011

(87) PCT Pub. No.: WO2010/003931
PCT Pub. Date: Apr. 14, 2010

(65) Prior Publication Data
US 2011/0213182 A1 Sep. 1, 2011

(30) Foreign Application Priority Data

Jul. 8, 2008 (EP) ...................................... 08159938

(51) Int. Cl.
*C07C 51/04* (2006.01)
*C07C 51/367* (2006.01)
*C07C 51/41* (2006.01)
*C07C 51/58* (2006.01)

(52) U.S. Cl.
CPC ............... *C07C 51/04* (2013.01); *C07C 51/367* (2013.01); *C07C 51/412* (2013.01); *C07C 51/58* (2013.01)

(58) Field of Classification Search
CPC .... C07C 51/04; C07C 51/367; C07C 51/412; C07C 51/58
USPC ....................................................... 562/586
See application file for complete search history.

(56) References Cited

U.S. PATENT DOCUMENTS

| | | | |
|---|---|---|---|
| 2,519,983 A | 8/1950 | Simons | |
| 2,713,593 A | 7/1955 | Brice et al. | |
| 3,271,341 A | 9/1966 | Garrison, Jr. | |
| 4,859,747 A | 8/1989 | Bierschenk et al. | |
| 4,987,254 A | 1/1991 | Schwertfeger et al. | |
| 2005/0090613 A1 | 4/2005 | Maruya et al. | |
| 2006/0199898 A1 | 9/2006 | Funaki et al. | |
| 2006/0281946 A1 | 12/2006 | Morita et al. | |
| 2007/0117915 A1 | 5/2007 | Funaki et al. | |
| 2007/0276068 A1* | 11/2007 | Hintzer et al. | 524/284 |
| 2008/0015304 A1 | 1/2008 | Hintzer et al. | |
| 2008/0200571 A1 | 8/2008 | Higuchi et al. | |
| 2008/0200627 A1 | 8/2008 | Funaki et al. | |
| 2008/0207859 A1 | 8/2008 | Matsuoka et al. | |
| 2008/0214714 A1 | 9/2008 | Hoshikawa et al. | |
| 2009/0306247 A1 | 12/2009 | Kawaguchi et al. | |

FOREIGN PATENT DOCUMENTS

| | | |
|---|---|---|
| EP | 354419 A1 | 2/1990 |
| JP | 2002317003 A | 10/2002 |
| JP | 2003119204 A | 4/2003 |
| JP | 2006321797 A | 11/2006 |
| JP | 2007119526 A | 5/2007 |
| JP | 2007283224 A | 11/2007 |
| WO | WO 9850603 A1 | 11/1998 |

(Continued)

OTHER PUBLICATIONS

Felling et al., Synthesis of perfluorinated functionalized, branch ethers, Journal of Fluorine Chemistry, 125, 749-754, 2004.*
Furin et al. Reaction of 1,1,2-trifluoro-2-hexafluoro-2'-(heptafluoropropoxy)-propoxyethylene with amines or alcohols, Journal of Fluorine Chemistry, 106, 13-24, 2000.*
Murotani et al. Synthesis and Polymerization of a Novel Perfluorinated Monomer, Journal of Fluorine Chemistry, 128, 1131-1136, 2007.*
Pardo et al., Fluorinated Analogues of tert-Butyl Alcohol as Novel Protecting Groups for Use in Fluorous Synthesis, Organic Letters, 3(23) 3711-3714, 2001.*
Wroblewska, A.., et al—"Synthesis of technically useful perfluorocarboxylic acids", Journal of Fluorine Chemistry, 2006, vol. 127, Elsevier B.V., pp. 345-350, 6 pgs.
Abe, T., et al—"Chapter I : Electrochemical Fluorination (Simons Process) as a Route to Perfluorinated Organic Compounds of Industrial Interest", 1982, Preparation, Properties, and Industrial Applications of Organofluorine Compounds, Edited by R.E. Banks,New York, Halsted Press, a division of John Wiley & Sons, pp. 19-43; 29 pgs.

(Continued)

*Primary Examiner* — Paul A Zucker
*Assistant Examiner* — Mark Luderer

(57) ABSTRACT

A process for the manufacture of a perfluorooxycarboxylate of formula (I): $R_fO-CF_2CF_2-O-CF_2-COOX_a$ (I), wherein $R_f$ is a perfluoro(oxy)alkyl group, and $X_a$ is H, a monovalent metal or an ammonium group of formula $NR^N_4$, with $R^N$, equal or different at each occurrence, being H or a $C_{1-6}$ hydrocarbon group, said process comprising: (A) reacting a perfluorovinylether of formula $R_f-O-CF=CF_2$ with an ethylene glycol derivative selected among ethylene glycol (HO—$CH_2CH_2$—OH), glycolic acid (HO—$CH_2$—COOH), glycolaldehyde (HO—$CH_2$—CHO) and protected derivatives thereof, so as to yield the corresponding addition product of formula $R_f-O-CFH-CF_2-O-CH_2-E$, and E being selected among —$CH_2OH$, —COOH and —CHO; (B) optionally protecting functional group E with suitable chemistry; (C) fluorinating the (protected) addition product to yield the corresponding perfluorinated addition product; (D) optionally deprotecting the perfluorinated addition product to yield corresponding acyl fluoride of formula $R_f-O-CF_2-CF_2-O-CF_2-C(O)F$; and (E) hydrolyzing and, optionally, neutralizing, the acyl fluoride for yielding the perfluorooxycarboxylate of formula (I).

12 Claims, No Drawings

(56) References Cited

FOREIGN PATENT DOCUMENTS

| WO | WO 0220676 A1 | | 3/2002 |
| WO | 2007/035734 | * | 3/2007 |
| WO | WO 2007046345 A1 | | 4/2007 |
| WO | WO 2007046377 A1 | | 4/2007 |
| WO | WO 2007046482 A1 | | 4/2007 |
| WO | WO 2007049517 A1 | | 5/2007 |
| WO | 2007/140091 | * | 12/2007 |
| WO | WO 2007140091 A1 | | 12/2007 |
| WO | WO 2008026767 A1 | | 3/2008 |

* cited by examiner

PROCESS FOR THE MANUFACTURE OF FLUOROSURFACTANTS

CROSS-REFERENCE TO RELATED APPLICATIONS

The present patent application is a U.S. national stage application under 35 U.S.C. §371 of International Application No. PCT/EP2009/058536, filed Jul. 7, 2009, which claims the benefit of European patent application no. 08159938.3, filed on Jul. 8, 2008, the whole content of this application being incorporated herein by reference for all purposes.

TECHNICAL FIELD

The invention pertains to an improved process for the manufacture of fluorinated surfactants having oxygen atoms in side chain.

BACKGROUND ART

Fluorinated surfactants are widely used in fluoropolymer manufacture for the stabilization of polymer dispersion in emulsion polymerization process.

Traditionally, perfluorocarboxylic acid derivatives have been commercially employed in said processes; due to environmental concerns related to the use of these materials, fluorosurfactants comprising oxygen atoms in side chain have attracted increasing attention for this application. Among them, perfluorooxycarboxylates of general formula: $R_fO—CF_2CF_2—O—CF_2—COOX$, with $R_f$ being a perfluoro(oxy) radical have been considered.

Among synthetic methods for manufacturing materials as above detailed, mention can be made of oligomerization of tetrafluoroethylene epoxide as described in U.S. Pat. No. 3,271,341 (E.I. DU PONT DE NEMOURS) 6 Sep. 1966. According to this method, tetrafluoroethylene epoxide is polymerized in the presence of a suitable free-radical forming compound (e.g. activated charcoal) at low temperature, resulting in polyethers having general formula: $CF_3CF_2—O—(CF_2CF_2—O)_n—CF_2COF$, with n being an integer from 0 to 10. Subsequent distillation affords various fractions differing in polymerization degree: corresponding acids or salts are obtained from acyl fluoride derivatives by hydrolysis and, for salts, simultaneous or subsequent reaction with a base. Nevertheless, this process suffers from the disadvantage that a distribution of polyether surfactants is obtained, so that yields towards a single particular target compound might be low and separation steps for isolating the same very burdensome.

JP 2006321797 (ASAHI GLASS CO LTD) 30 Nov. 2006 discloses a process for the manufacture of perfluorocarboxylates of formula $R^F—(O—CF_2CF_2)_{k-1}—CF_2—COOH$, with $R^F$ being a perfluoroalkyl group, and k being an integer ≥1, by a multi-step process comprising:

(i) esterification of a hydrogenated compound of formula: $R—(O—CH_2CH_2)_k—OH$, with R being a $C_{1-10}$ hydrocarbon group with a fluorinated (poly)acyl fluoride of formula $Q(COF)_n$ (Q being a n-valent hydrocarbon group; n≥1) yielding corresponding ester of formula: $Q[C(O)—O—(CH_2CH_2O)_k—R]_n$;

(ii) complete fluorination of all C—H bonds in C—F bonds of this latter to yield corresponding perfluorinated compound of formula $Q^F[C(O)—O—(CF_2CF_2O)_k—R^F]_n$;

(iii) decomposition of the perfluoroester to yield perfluoroacyl compound of formula $F—C(O)—CF_2O—(CF_2CF_2O)_{k-1}—R^F$;

(iv) hydrolysis and/or treatment with a base for yielding corresponding carboxylate salt.

Major drawback of this process is its significant consumption of fluorine in fluorination step, as raw material providing backbone of the final perfluorocarboxylates is initially provided as fully hydrogenated precursor, so that severe fluorination conditions are required for assuring quantitative fluorination towards the target compound.

Scientific paper from WROBLEWSKA, A., et al. Synthesis of technicall useful perfluorocarboxylic acids. *Journal of Fluorine Chemistry*. 2006, vol. 127, p. 345-350. discloses a process for manufacturing perfluorocarboxylic acids via dehydroiodination of perfluoroalkylethene iodides and subsequent oxidation of ethylenically unsaturated intermediate therefrom.

WO 2007/014009 (3M INNOVATIVE PROPERTIES COMPANY) 6 Dec. 2007 discloses surfactants of formula $[R_fO-L-COO^-]_xX^{i+}$, wherein L is a linear partially or fully fluorinated alkylene group or aliphatic hydrocarbon group and $R_f$ is a linear partially or fully fluorinated aliphatic group interrupted with one or more oxygen atoms, $X^{i+}$ represents a cation having the valence i=1, 2 or 3. Certain surfactants encompassed by above mentioned formula can be prepared by reacting certain fluorinated olefins with a hydrocarbon alcohol in an alkaline medium, and then decomposing the resulting ether in acidic conditions thereby forming the corresponding carboxylic acid. Among suitable alcohols, mention is made of methanol, ethanol, butanol. Nevertheless, this process does not enable manufacture of fully fluorinated carboxylates.

It was thus felt a need in the art for providing a novel process for manufacturing perfluorooxycarboxylates of general formula: $R_fO—CF_2CF_2—O—CF_2—COOX$, which could override drawbacks of the prior art.

DISCLOSURE OF INVENTION

It is thus an object of the present invention a process for the manufacture of a perfluorooxycarboxylate of formula (I):

$$R_fO—CF_2CF_2—O—CF_2—COOX_a \qquad (I)$$

wherein $R_f$ is a perfluoro(oxy)alkyl group, and $X_a$ is H, a monovalent metal or an ammonium group of formula $NR^N_4$, with $R^N$, equal or different at each occurrence, being H or a $C_{1-6}$ hydrocarbon group, said process comprising:

(A) reacting a perfluorovinylether of formula $R_f—O—CF=CF_2$ with an ethylene glycol derivative selected among ethylene glycol (HO—$CH_2CH_2$—OH), glycolic acid (HO—$CH_2$—COOH), glycolaldehyde (HO—$CH_2$—CHO) and protected derivatives thereof, so as to yield the corresponding addition product of formula $R_f—O—CFH—CF_2—O—CH_2-E$, with $R_f$ having the same meaning as above detailed, and E being selected among —$CH_2OH$, —COOH and —CHO;

(B) optionally protecting functional group E with suitable chemistry;

(C) fluorinating said (protected) addition product to yield the corresponding perfluorinated addition product;

(D) optionally deprotecting said perfluorinated addition product to yield corresponding acyl fluoride of formula $R_f—O—CF_2—CF_2—O—CF_2—C(O)F$;

(E) hydrolyzing and, optionally, neutralizing, said acyl fluoride for yielding the perfluorooxycarboxylate of formula (I).

The Applicant has found that by means of the synthetic method hereby described it is advantageously possible to synthesize target compounds by significantly reducing fluorine consumption in the fluorination step and obtaining target compounds in high yields.

In perfluorovinylether of formula $R_f$—O—CF=$CF_2$, $R_f$ can be notably a $C_{1-6}$ perfluoroalkyl group or a $C_{1-6}$ perfluorooxyalkyl group comprising one or more than one catenary oxygen atoms.

Non limitative examples of perfluorovinylethers suitable to the purposes of the invention are notably perfluoroalkylvinyl ethers selected among perfluoromethylvinyl ether ($CF_3$—O—CF=$CF_2$), perfluoroethylvinyl ether ($CF_3CF_2$—O—CF=$CF_2$), perfluoropropylvinyl ether ($CF_3CF_2CF_2$—O—CF=$CF_2$); and perfluorooxyalkylvinyl ethers selected among $CF_3O$—$CF_2CF_2CF_2O$—CF=$CF_2$, $CF_3CF_2O$—$CF_2$—O—CF=$CF_2$; $CF_3OCF_2CF_2O$—$CF_2$—O—CF=$CF_2$; $CF_3O$—$CF_2$—O—CF=$CF_2$.

Perfluoroethylvinyl ether is particularly preferred as it enables obtaining compound $CF_3CF_2O$—$CF_2CF_2$—O—$CF_2$—$COOX_a$, with $X_a$ having the meaning as above defined (i.e. (I) wherein $R_f$ is $CF_3CF_2$—), which is particularly useful as surfactant in fluoromonomer emulsion polymerization.

The choice of the ethylene glycol derivative among those above mentioned is not critical; nevertheless, chemistry of the functional group present in this derivative in addition to the hydroxyl function will determine appropriate selection of the protecting group in the further steps of the process of the invention.

According to a first embodiment of the invention, in step (A) the vinyl ether is reacted with ethylene glycol so as to yield a hydroxyl adduct (III). Reaction can thus be sketched as follows:

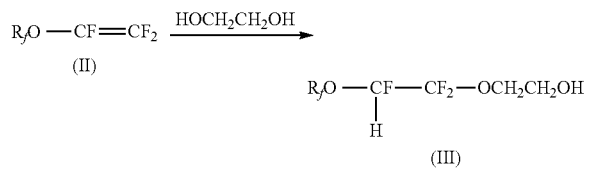

wherein $R_f$ has the meaning as above defined.

Addition reaction is generally carried out in the presence of a base, typically in an aqueous reaction medium. As bases, metal hydroxides, ammonia or amines can be mentioned, alkaline metal hydroxides being preferred. In order to maximize yield towards mono-addition product, the amount of base is generally adapted so that 1 equivalent of base is used per mole of vinyl ether (II), so that statistically, only one hydroxyl group of the ethylene glycol molecule is advantageously activated towards addition onto the double bond of (II).

In step (B) according to this first embodiment of the invention, the hydroxyl free group of the hydroxyl adduct (III) is protected with a suitable protecting group stable under fluorination conditions, so as to yield the corresponding protected hydroxyl adduct (IV):

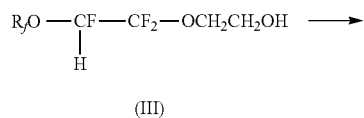

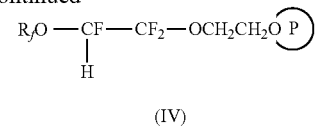

wherein the P round circle stands for a protective group.

Among preferred protecting groups, mention can be notably made of the ester group. Thus, in a variant of step (B) of this embodiment, the hydroxyl adduct (III) is preferably reacted with a carboxyl derivative of formula $R_c$—CO—$X_c$ (with $X_c$ being a halogen or an —OH group and $R_c$ being a hydrocarbon group, optionally (per)fluorinated, optionally bearing one or more additional —CO—$X_c$ group(s)) so as to yield corresponding ester as sketched in following scheme:

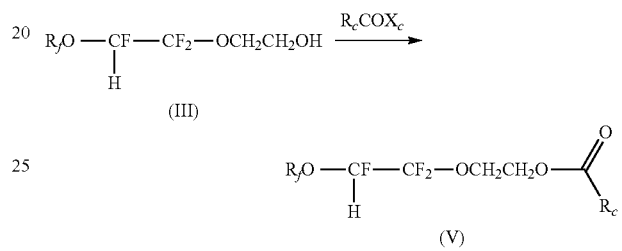

wherein $R_f$, $R_c$ and $X_c$ have the meanings as above defined. Typically, the carbonyl derivative $R_c$—CO—$X_c$ will be selected among perfluorinated mono-acyl or di-acyl fluorides (i.e. compounds wherein X, is fluorine and $R_c$ is a perfluorocarbon group, optionally comprising an additional —COF group). Non limitative examples carbonyl derivatives suitable for the purposes of the invention are notably $CF_3$—C(O)F, $(CF_3)_2CF$—C(O)F, $CF_3CF_2CF_2O$—$CF(CF_3)CF_2O$—CF($CF_3$)—C(O)F, FC(O)—CF($CF_3$)—O—CF($CF_3$)—C(O)F.

In step (C) the protected hydroxyl adduct (IV) according to this first embodiment is fluorinated to yield the corresponding perfluorinated addition product, as depicted in the following scheme:

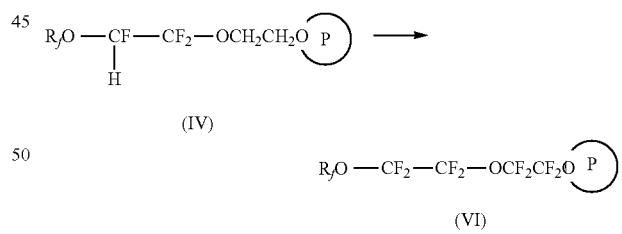

wherein $R_f$ and P round circle have the meanings as above defined. Fluorination is generally carried out in the presence of a fluorine source, typically in the presence of molecular fluorine. In case of direct fluorination, a hydrogen fluoride scavenger (e.g. NaF, KF) can be used as taught in U.S. Pat. No. 4,859,747 (EXFLUOR RESEARCH CORPORATION) 22 Aug. 1989. As an alternative, fluorination can be accomplished by ABE, T., et al. Preparation, properties, and industrial applications of organofluorine Compounds. Edited by R. E. BANKS. New York: Halsted, 1982. p. 19-43.

When the hydroxyl group has been protected by formation of an ester moiety, then the fluorination of step (C) proceeds as follows:

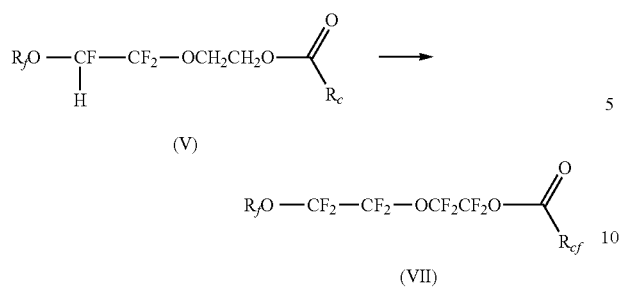

(V)

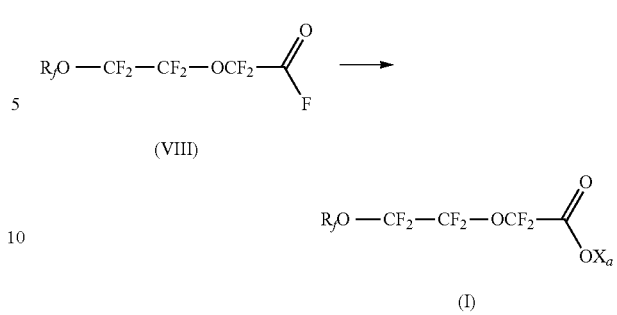

(VIII)

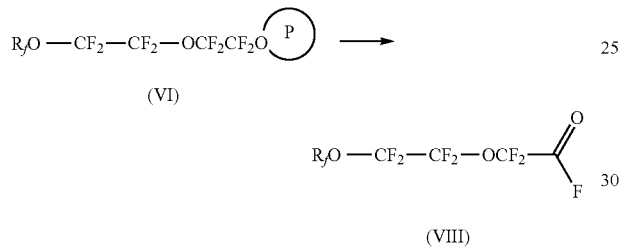

(VII)

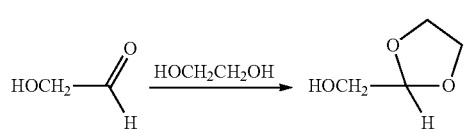

(I)

wherein $R_f$ and $R_c$ have the meanings as above defined and $R_{cf}$ is the perfluorinated equivalent of group $R_c$; it is also understood that should $R_c$ be perfluorinated, $R_{cf}$=$R_c$.

In subsequent step (D), said perfluorinated addition product (VI) of this first embodiment is deprotected to yield corresponding acyl fluoride of formula $R_f$—O—$CF_2$—$CF_2$—O—$CF_2$—C(O)F:

$R_fO$—$CF_2$—$CF_2$—$OCF_2CF_2O$—(P) ⟶

(VI)

$R_fO$—$CF_2$—$CF_2$—$OCF_2$—C(O)F (VIII)

wherein $R_f$ and P round circle have the same meanings as above defined. Reaction conditions enabling decomposition and/or hydrolysis of the protective group to yield the corresponding acyl fluoride would generally depend upon the chemistry of said protecting group. The skilled of the art will select appropriate reactants and conditions which would be suitable for deprotecting outstanding protective group.

When the hydroxyl function has been protected with formation of an ester moiety, in step (D), acyl fluoride can be notably obtained by thermolysis in the presence of metal fluorides, in particular in the presence of NaF, $CaF_2$, AgF, CsF, KF, preferably KF, as sketched here below:

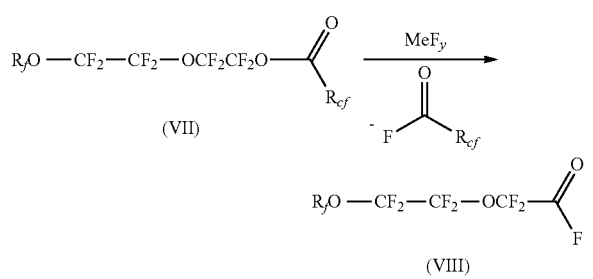

(VII)

(VIII)

wherein $R_f$, Rd have the meanings as above defined; Me is a metal having y valence, y is 1 or 2.

Hydrolysis and, optionally, neutralization of acyl fluoride (VIII) in step (E) can be performed by standard methods well known to those skilled in the art, for obtaining the perfluorooxycarboxylate of formula (I):

with $R_f$ and $X_a$ having the meanings as above defined.

According to a second embodiment of the invention, in step (A) the vinyl ether is reacted with glycolaldehyde (HO—$CH_2$—CHO) so as to yield an aldehyde adduct (X). Reaction is generally carried out by preliminarily protecting the aldehyde function of the glycolaldehyde and then reacting said protected glycolaldehyde with perfluorovinylether (II), and finally deprotecting aldehyde functionality, so as to obtain aldehyde adduct as sketched here below:

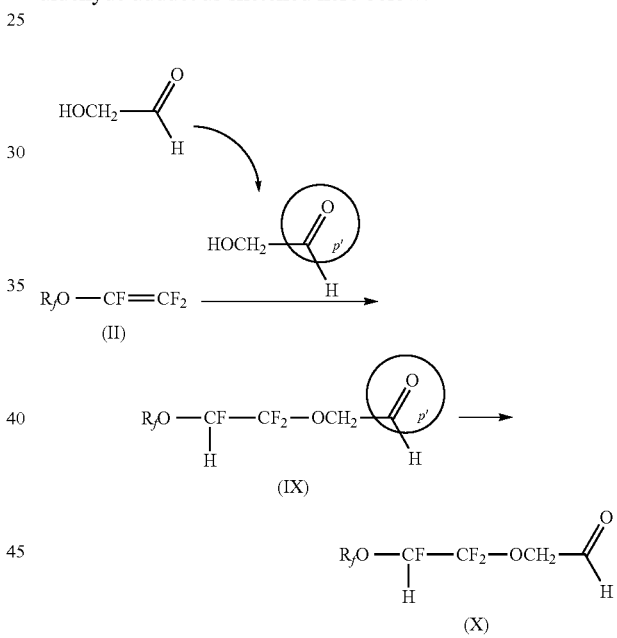

wherein $R_f$ has the meaning as above defined and the round circle p' stands for a protective group for aldehyde group.

While the choice of the protective group is not particularly limited, provided that it is stable under reaction conditions of the addition reaction onto vinyl ether (II) for yielding (IX), it is generally preferred to protect the glycolaldehyde by formation of a cyclic acetal, more preferably by reaction with ethylene glycol, as depicted here below:

Protected aldehyde adduct will in this preferred variant comply with formula (XI) here below:

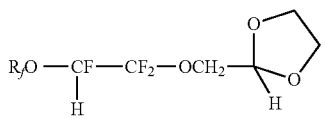
(XI)

which can yield under hydrolysis conditions, typically in acidic aqueous medium, the target aldehyde adduct compound (X).

In step (B) of this second embodiment, the aldehyde group is typically protected by oxidation towards corresponding acid compound, and subsequent transformation either in acid halide or in ester, as sketched herein below:

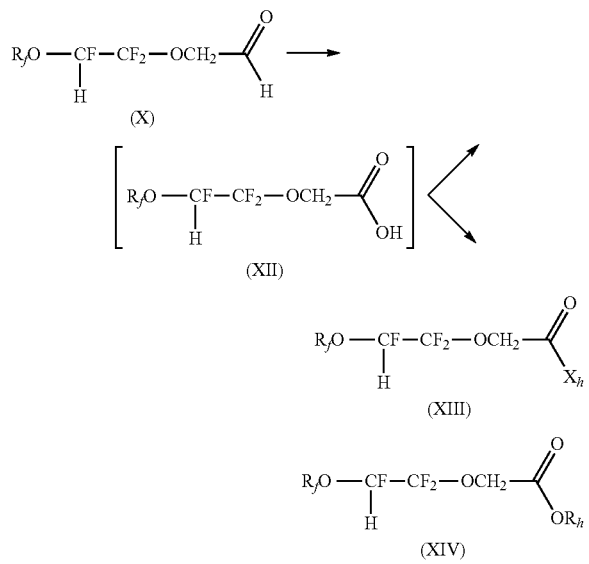

wherein $R_f$ has the meaning as above defined, $X_h$ is a halogen, preferably selected among F and Cl, $R_h$ is a hydrocarbon group, preferably a $C_{1-6}$ alkyl group, e.g. —$CH_3$.

Acid halide (XIII) is generally obtained by standard method, e.g. reacting corresponding acid compound with a thionyl halide.

Esterification to yield compound (XIV) can be accomplished by reaction of the corresponding acid with an alcohol under basic conditions and/or by reaction of the same with an alcoholate. Reaction with methanol or alkaline metal methylates (e.g. $CH_3ONa$ is preferred).

Acid halides (XIII) and/or esters (XIV) undergo advantageously fluorination in step (C) of the process of this second embodiment.

Fluorination of these compounds can be accomplished by standard methods which are well known to the skilled in the art. This latter will select appropriate fluorination techniques and conditions under which while the backbone of protected aldehyde adduct is advantageously completely fluorinated, ester moieties are e.g. preserved and acyl halides transformed in acyl fluorides, as sketched in scheme here below:

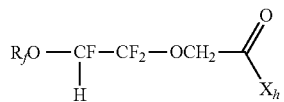
(XIII)

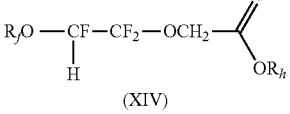
(XIV)

fluorination →

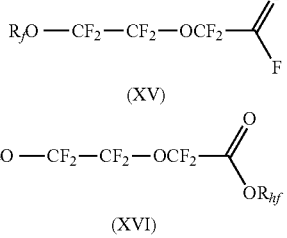
(XV)

(XVI)

wherein $R_f$, $R_h$ and $X_h$ have the same meaning as above detailed, and $R_{hf}$ is the perfluorinated counterpart of $R_h$, wherein all C—H bonds have been changed into C—F bonds.

As non limitative examples of techniques suitable to the purpose of the invention, mention can be made of Simons electrochemical fluorination, as described notably in U.S. Pat. No. 2,519,983 (MINNESOTA MINING & MANUFACTURING COMPANY) 22 Aug. 1950, U.S. Pat. No. 2,713,593 (MINNESOTA MINING & MANUFACTURING COMPANY) 19 Jul. 1955, WO 98/50603 (MINNESOTA MINING & MANUFACTURING COMPANY) 12 Dec. 1998, and of direct fluorination, in the presence of elemental fluorine, optionally in combination with a suitable HF scavenger, as taught in U.S. Pat. No. 4,859,747 (EXFLUOR RESEARCH CORPORATION) 22 Aug. 1989.

In step (D) of this embodiment, perfluorinated compound obtained from fluorination (like, e.g. compounds XV or XVI) is decomposed to yield acyl fluoride.

It is understood that in case of protection of the aldehyde as an acyl halide, deprotection of this group to yield acyl fluoride is directly obtained in fluorination conditions.

In case of protection as an ester, the perfluoro ester from fluorination is generally worked up as already described for the first embodiment of the invention.

Involved chemistry in subsequent steps required for obtaining target perfluorooxycarboxylate of formula (I) from acyl fluoride have been already detailed with reference to the description of the first embodiment of the invention.

According to a third embodiment of the invention, in step (A) the vinyl ether is reacted with glycolic acid (HO—$CH_2$—COOH) so as to yield an acid adduct (XIII):

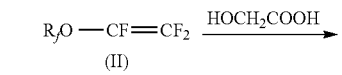

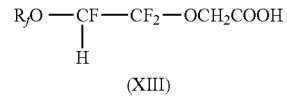
(XIII)

Reaction is typically carried out in the presence of a base, typically in an aqueous reaction medium. As bases, metal hydroxides, ammonia or amines can be mentioned, alkaline metal hydroxides being preferred. The amount of base is generally adapted so that at least 2 equivalents of base are used per mole of glycolic acid, so that an intermediate carboxylate adduct (XVII) is generally formed, which yields by acidification the target acid (XIII), as depicted herein below:

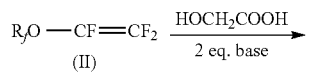
(II)

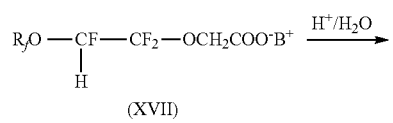
(XVII)

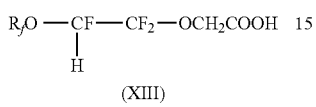
(XIII)

wherein $R_f$ has the same meaning as above defined, and $B^+$ is the couter-cation of the base used in the addition step (e.g. $Na^+$, $K^+$, $NH_4^+$ and the like).

Relevant chemistry and variants of subsequent steps according to this third embodiment have been already described with reference to the second embodiment of this invention, to which is made reference here.

The invention will be now described in more detail with reference to the following examples, whose purpose is merely illustrative and not intended to limit the scope of the invention.

EXAMPLE 1

Synthesis of $CF_3CF_2$—O—$CF_2CF_2$—O—$CF_2COONH_4$ from ethylene glycol

Ex. 1 (a) Addition of Ethylene Glycol to Perfluoroethylvinyl Ether

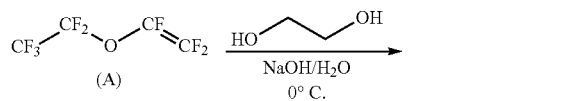
(A)

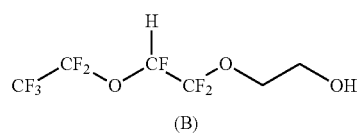
(B)

In a four necked, round-bottomed glass reactor, equipped with magnetic stirrer, thermometer, condenser maintained at −75° C. and two dropping funnels, 150 g of ethylene glycol were introduced; a solution of 13.8 g (346 mmoles) of NaOH in 67 ml of water were then added while maintaining a temperature of 0° C. The 75 g (346 mmoles) of perfluoroethylvinyl ether ($CF_2$=$CF$—O—$C_2F_5$) were slowly added. The mixture was then stirred at room temperature for 2 hours. After addition of 190 ml of tetrahydrofuran (THF), organic phase was recovered, dried over $MgSO_4$, filtered and purified by fractional distillation.

72 g of target compound of formula (B) having boiling point=143° C. at 760 mmHg were collected, corresponding to a yield of 75% moles.

Ex. 1 (b) Protection of the Adduct (B) Via Esterification with Acetyl Fluoride

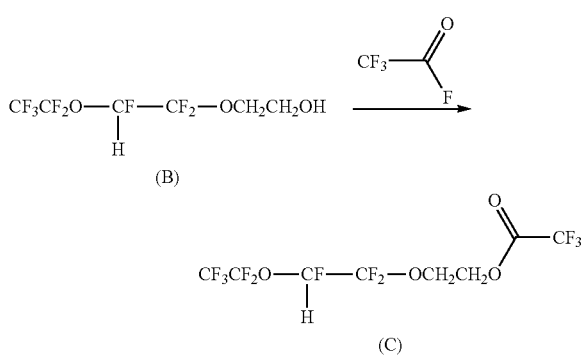
(B)

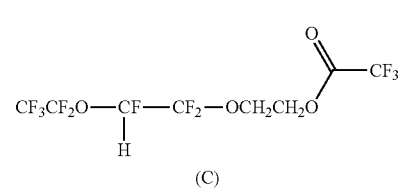
(C)

The alcohol adduct (B) is diluted in 200 ml of A113 and 16 g of powdered NaF are added; then keeping the temperature at 0° C., 45 g of $CF_3COF$ are slowly added to the solution. After removal of solid HF scavenger, the ester (C) was recovered and used in subsequent fluorination without further purification.

Ex. 1 (c) Fluorination of the Ester (C)

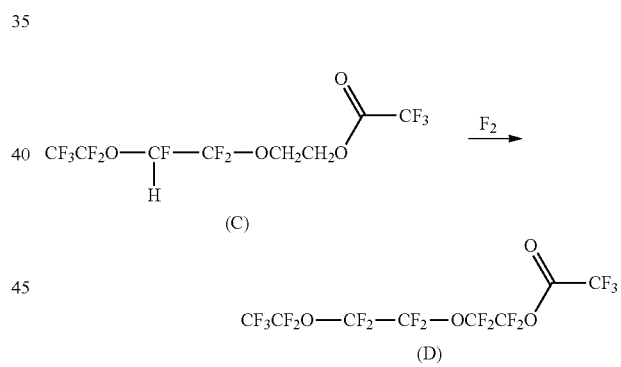
(C)

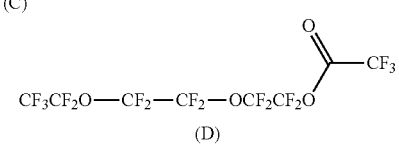
(D)

The filtered solution of (C) is then treated with fluorine (diluted in nitrogen $F_2$:$N_2$=20:80) at 0-20° C.; reaction was monitored by gas chromatography. Once fluorination completed, the crude mixture was fractionally distilled obtaining the perfluorinated ester (D) (84 g Yield 70%).

Ex. 1 (d) Decomposition of the Perfluoroester (D)

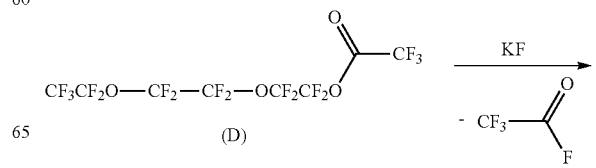
(D)

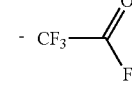

-continued

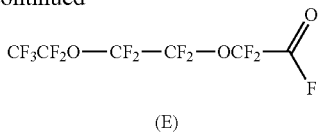

(E)

The perfluoroester (D) was quantitatively decomposed to CF$_3$COF and compound (E) by treatment with KF at a temperature of about 100° C.; the acyl fluoride (E) was recovered by fractional distillation.

Ex. 1 (e) Hydrolysis and Neutralization of the Acyl Fluoride (E)

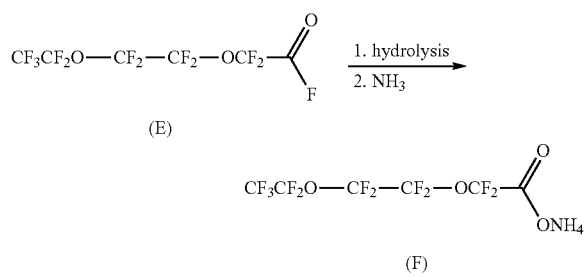

The acyl fluoride (E) was hydrolyzed quantitatively to the corresponding acid with water; after removal of HF by nitrogen bubbling, mixture was fractionally distilled for recovering free acid. A CH$_2$Cl$_2$ solution of said acid was contacted with gaseous ammonia for precipitating ammonium salt, which was recovered by filtration and drying.

EXAMPLE 2

Synthesis of CF$_3$CF$_2$—O—CF$_2$CF$_2$—O—CF$_2$COONH$_4$ from glycol aldehyde

Ex 2 (a) Addition of Glycol Aldehyde to the Perfluoroethylvinyl Ether

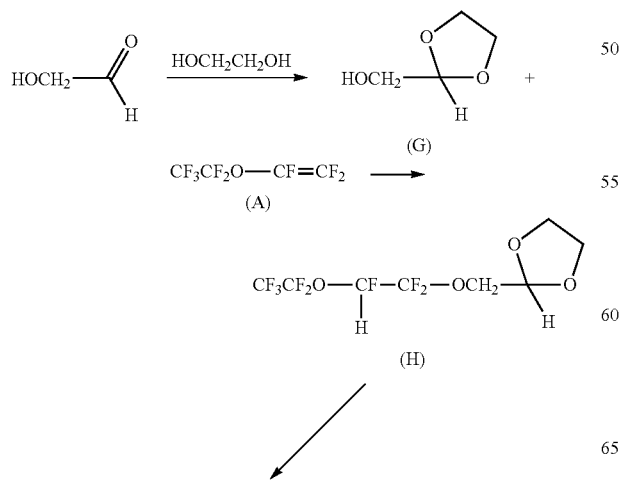

-continued

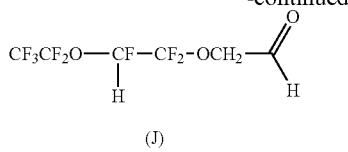

(J)

In a four necked round-bottomed glass reactor, equipped with magnetic stirrer, thermometer, condenser maintained at −75° C. (dry ice-Isopropyl alcohol) and two addition funnels, 60 g of glycol aldehyde (1.0 mol) and 62 g of ethylene glycol (1.0 mol) were loaded, followed by 10 g of 37% HCl water solution (0.10 mol HCl) at room temperature; after 1 hour under stirring, the formation of cyclic acetal (G) was complete; the reactor was thus cooled to 0° C. with an ice water bath, then a solution of 44 g (1.1 mol) of NaOH (s) and 44 ml of distilled water H$_2$O was added in half an hour. After a slight exothermicity, at 0° C., 216 g (1.0 mmol) of (A) were slowly added. At the end of the addition, the reaction mixture was allowed to reach 20° C., and stirred for another 2 hours. The crude mixture was extracted three times with tetrahydrofuran (THF). The combined THF extracts were dehydrated with MgSO$_4$, filtered and fractionally distilled, collecting 247 g of the partially hydrogenated ether (H) (yield 77% mol). The aldehyde group of adduct (H) was deprotected (quantitatively) obtaining the corresponding aldehyde (J) by hydrolysis in acidic conditions (diluted HCl).

Ex 2 (b) Protection of the Aldehyde as Ester Group

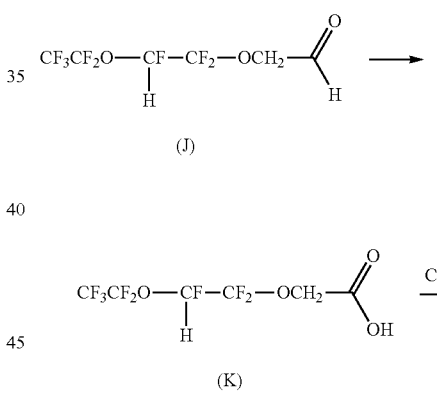

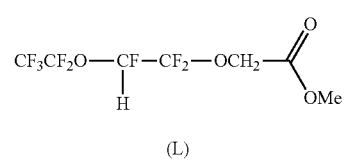

(L)

So-obtained aldehyde (J) was oxidized with a basic solution of potassium permanganate at 90° C. for four hours; the solution was filtered to remove MnO$_2$ and then treated with 37% HCl water solution up to pH=1. The acid was recovered by washing with CH$_2$Cl$_2$, treating with MgSO$_4$, filtering and evaporating the CH$_2$Cl$_2$. 135 g of the acid (K) were obtained (yield 60% mol). The acid was then treated with a solution of MeONa/MeOH (5% excess) at room temperature; after distillation, 134 g of the ester (L) were obtained (yield 95% mol)

13
Ex 2 (c) Fluorination of the Protected Aldehyde Adduct as Ester (L)

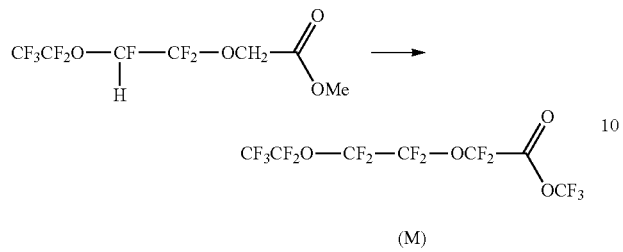

(M)

The ester (L) was diluted with 500 ml of A113 and then fluorine diluted with nitrogen (20:80) was introduced under stirring at 0-20° C. following the H to F conversion by GC; when the fluorination was completed, crude mixture was fractionally distilled obtaining 130 g of the perfluorinated ester (M) (yield 72% mol).

Ex 2 (d) Hydrolysis of Ester (M) for Yielding Acyl Fluoride (E)

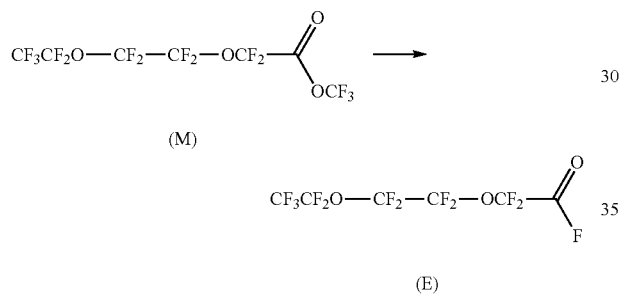

The perfluorinated ester (M) was quantitatively decomposed to acyl fluoride (N) by treatment with KF at a temperature of about 80° C.; the latter acyl fluoride was recovered by fractional distillation.

Ex. 2 (e) Hydrolysis and Neutralization of the Acyl Fluoride (E)

Same procedure as detailed in step Ex. 1(e) was repeated for obtaining ammonium salt (F).

EXAMPLE 3

Synthesis of $CF_3CF_2$—O—$CF_2CF_2$—O—$CF_2COONH_4$ from glycolic acid

Ex. 3(a) Addition of Glycolic Acid to the Perfluoroethylvinyl Ether

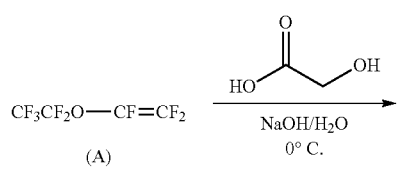

14

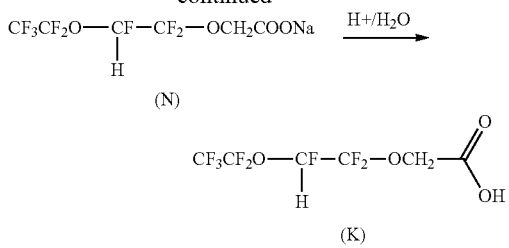

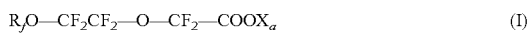

(K)

In a four necked round-bottomed glass reactor, equipped with magnetic stirrer, thermometer, condenser maintained at -75° C. (dry ice-Isopropyl alcohol) and two addition funnels, 76 g of glycolic acid (1.0 mol) were loaded, followed by a solution of 84 g (2.1 mol) of NaOH (s) in 300 ml of distilled water $H_2O$; the reactor was cooled to 0° C. with an ice water bath. 216 g (1.0 mol) of $CF_2$=$CFOCF_2CF_3$ were slowly added. At the end of the addition the reaction mixture was allowed to reach 20° C., and stirred for another 3 hours. Then suitable amounts of a 37% HCl water solution were added until achieving a pH=1. The acidified mixture was then extracted three times with THF. Combined THF phases were dehydrated with $MgSO_4$, filtered and fractionally distilled for recovering acid adduct (K). 215 g of the partially hydrogenated acid adduct (K) were collected (yield 74% mol).

Same procedure as above detailed in sections Ex. 2(b), Ex. 2(c) and Ex. 2(d) was followed for obtaining ammonium salt (F) from intermediate (K).

The invention claimed is:

1. A process for the manufacture of a perfluorooxycarboxylic acid or perfluorooxycarboxylate of formula (I):

$$R_fO—CF_2CF_2—O—CF_2—COOX_a \quad (I)$$

wherein $R_f$ is a perfluoro(oxy)alkyl group, and $X_a$ is H, a monovalent metal or an ammonium group of formula $NR^N_4$, with $R^N$, equal or different at each occurrence, being H or a $C_{1-6}$ hydrocarbon group, said process comprising:

(A) reacting a perfluorovinylether of formula $R_f$—O—CF=$CF_2$ with an ethylene glycol derivative selected from the group consisting of ethylene glycol (HO—$CH_2CH_2$—OH), glycolaldehyde (HO—$CH_2$—CHO), and protected derivatives thereof, so as to yield the corresponding addition product of formula $R_f$—O—CFH—$CF_2$—O—$CH_2$-E, with $R_f$ having the same meaning as defined in formula (I), and E being selected from the group consisting of —$CH_2OH$, —COOH, and —CHO;

(B) optionally protecting functional group E;

(C) fluorinating said addition product to yield the corresponding perfluorinated addition product;

(D) optionally deprotecting said perfluorinated addition product to yield corresponding acyl fluoride of formula $R_f$—O—$CF_2$—$CF_2$—O—$CF_2$—C(O)F; and (E) hydrolyzing and, optionally, neutralizing, said acyl fluoride for yielding the perfluorooxycarboxylic acid or perfluorooxycarboxylate of formula (I).

2. The process of claim 1, wherein in step (A) the vinyl ether is reacted with ethylene glycol so as to yield a hydroxyl adduct (III):

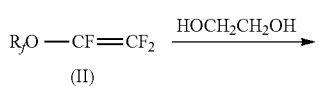

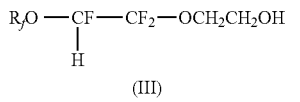

$R_f$ has the same meaning as defined in claim 1.

3. The process of claim 2, wherein in step (B) the hydroxyl free group of the hydroxyl adduct (III) is protected with a protecting group stable under fluorination conditions, so as to yield the protected hydroxyl adduct of formula (IV):

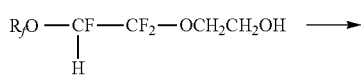

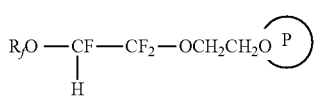

wherein the P round circle stands for a protective group, and $R_f$ has the same meaning as defined in claim 1.

4. The process of claim 3, wherein in step (B) the hydroxyl adduct (III) is reacted with a carboxyl derivative of formula $R_c$—CO—$X_c$ with $X_c$ being a halogen or an —OH group and $R_c$ being a hydrocarbon group, optionally (per)fluorinated, optionally bearing one or more additional —CO—$X_c$ group(s) so as to yield the ester of formula (V):

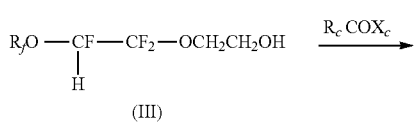

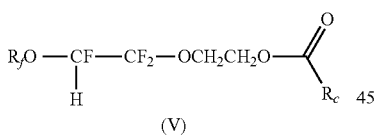

$R_f$ has the same meaning as defined in claim 1 and $R_c$ and $X_c$ have the meanings as above defined.

5. The process of claim 3, wherein in step (C) the protected hydroxyl adduct (IV) is fluorinated to yield the perfluorinated addition product of formula (VI):

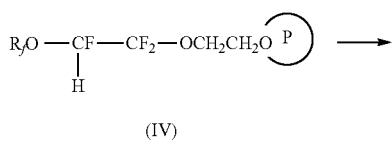

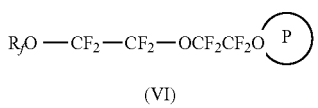

$R_f$ and P round circle have the same meanings as defined in claim 3.

6. The process of claim 4, wherein in step (C) the ester of formula (V) is fluorinated to form the perfluorinated ester of formula (VII):

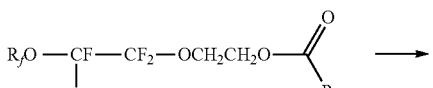

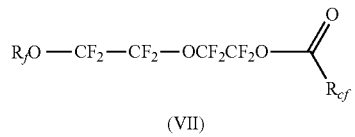

$R_f$ and $R_c$ have the same meanings as defined in claim 4 and $R_{cf}$ is the perfluorinated equivalent of group $R_c$; being also understood that should $R_c$ be perfluorinated, $R_{cf}$=$R_c$.

7. The process of claim 5, wherein in subsequent step (D), said perfluorinated addition product (VI) is deprotected to yield the acyl fluoride of formula (VIII):

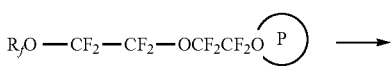

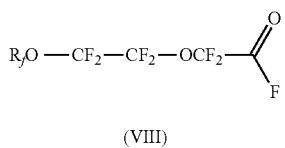

$R_f$ and P round circle have the same meanings as defined in claim 5.

8. The process of claim 6, wherein in step (D), the acyl fluoride of formula (VIII) is obtained by thermolysis of the perfluorinated ester of formula (VII) in the presence of metal fluoride MeF$_y$:

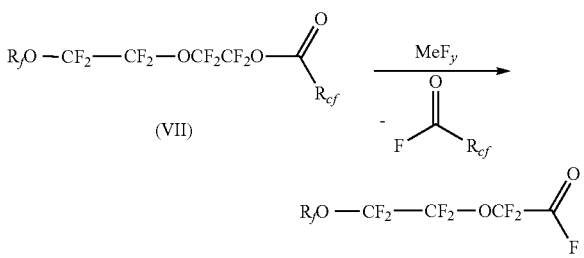

$R_f$, $R_{cf}$ have the same meanings as defined in claim 6; Me is a metal having y valence, y being 1 or 2.

9. The process of claim 1, wherein in step (A) the vinyl ether is reacted with glycolaldehyde (HO—CH$_2$—CHO) so as to yield an aldehyde adduct (X).

10. The process of claim 9, wherein the addition reaction of step (A) is carried out by preliminarily protecting the aldehyde function of the glycolaldehyde and then reacting said protected glycolaldehyde with perfluorovinylether (II), and finally deprotecting aldehyde functionality, so as to obtain the aldehyde adduct of formula (X):

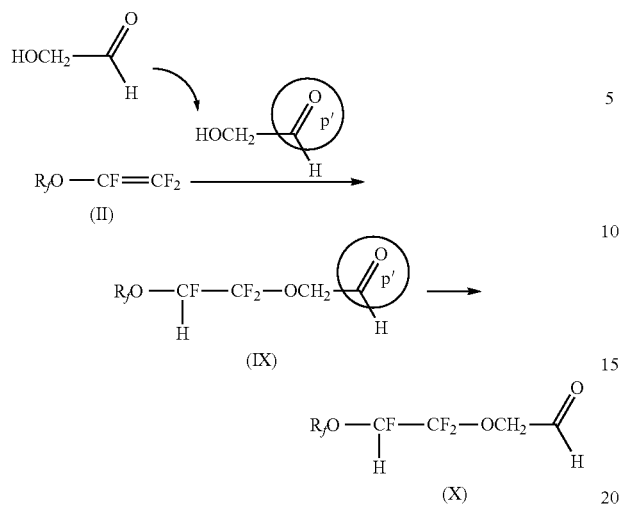

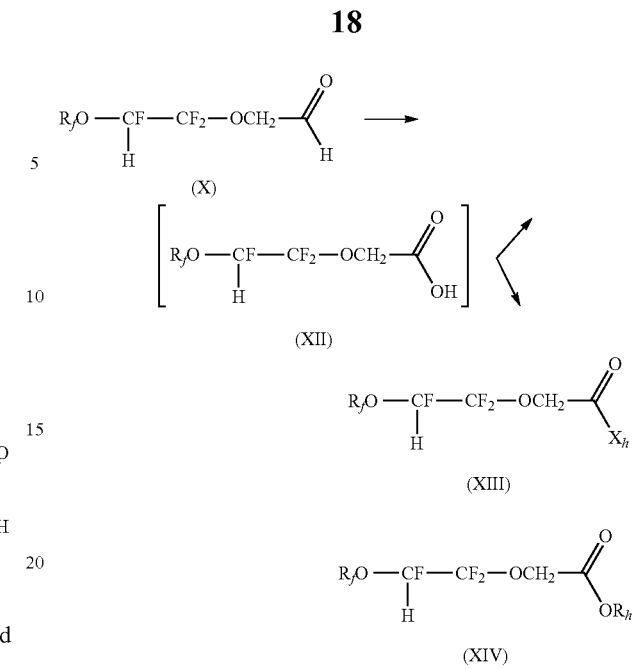

$R_f$ has the same meaning as defined in claim 1 and the round circle p' stands for an aldehyde protecting group.

11. The process of claim 10, wherein in step (B), the aldehyde group of the aldehyde adduct of formula (X) is protected by oxidation to form the acid compound of formula (XII), and subsequently transformed either in acid halide to form a compound of formula (XIII) or in ester to form a compound of formula (XIV):

$R_f$ has the same meaning as defined in claim 10, $X_h$ is a halogen, and $R_h$ is a hydrocarbon group.

12. The process of claim 11, wherein $X_h$ is selected from F and Cl and $R_h$ is —$CH_3$.

\* \* \* \* \*